United States Patent [19]
Kriegler et al.

[11] Patent Number: 5,639,593
[45] Date of Patent: Jun. 17, 1997

[54] METHOD FOR DETERMINING TNF

[75] Inventors: Michael Kriegler, San Francisco; Danute E. Nitecki, Berkeley, both of Calif.

[73] Assignee: Cetus Oncology Corporation, Emeryville, Calif.

[21] Appl. No.: 649,197

[22] Filed: May 17, 1996

Related U.S. Application Data

[63] Continuation of Ser. No. 385,434, Feb. 8, 1995, Pat. No. 5,545,518, which is a continuation of Ser. No. 53,558, Apr. 26, 1993, Pat. No. 5,422,425, which is a continuation of Ser. No. 562,720, Aug. 6, 1990, abandoned.

[51] Int. Cl.$^6$ .................... C12Q 1/37; C07K 7/02; C07K 14/81
[52] U.S. Cl. .................. 435/4; 435/7.4; 435/7.8; 435/23; 435/219; 435/963; 530/324; 530/326; 530/332; 530/351
[58] Field of Search .................. 530/324, 326, 530/332, 351; 435/4, 7.4, 7.8, 23, 219, 963

[56] References Cited

U.S. PATENT DOCUMENTS

| | | | |
|---|---|---|---|
| 4,190,496 | 2/1980 | Rubenstein et al. | 435/7.9 |
| 4,323,647 | 4/1982 | Monji et al. | 435/5 |
| 4,677,063 | 6/1987 | Mark et al. | 435/69.5 |
| 4,766,069 | 8/1988 | Auron et al. | 435/69.52 |
| 4,808,611 | 2/1989 | Cosman | 514/12 |
| 4,859,600 | 8/1989 | Gray et al. | 435/252.33 |
| 4,892,813 | 1/1990 | Cohen et al. | 435/4 |
| 4,897,444 | 1/1990 | Brynes et al. | 525/54.1 |
| 4,923,802 | 5/1990 | Gallis | 435/15 |
| 5,138,035 | 8/1992 | Wakselman et al. | 530/317 |
| 5,231,105 | 7/1993 | Shoji et al. | 514/325 |
| 5,242,904 | 9/1993 | Kettner et al. | 514/18 |
| 5,250,681 | 10/1993 | Shoji et al. | 540/577 |
| 5,288,612 | 2/1994 | Griffin et al. | 435/23 |
| 5,422,425 | 6/1995 | Kriegler et al. | 530/324 |
| 5,545,518 | 8/1996 | Kriegler | 435/4 |

FOREIGN PATENT DOCUMENTS

| | | |
|---|---|---|
| 288 088 | 10/1988 | European Pat. Off. |
| 351 789 | 1/1990 | European Pat. Off. |
| 308 378 | 11/1994 | European Pat. Off. |
| 9003577 | 4/1990 | WIPO |
| 90/03577 | 4/1990 | WIPO |
| 90/06940 | 6/1990 | WIPO |
| 91/02078 | 2/1991 | WIPO |

OTHER PUBLICATIONS

Cseh et al. "Alternative Cleavage of the Cachectin/TNF Propeptide Results in a Larger Inactive Form of Secreted Protein" JBL 264 16256–16260 1989.

Tracey et al., "Ant–cachectin/TNF monoclonal antibodies prevent septic shock during lethal bacteraemia," *Nature*, 330:662–664 (Dec. 17, 1987).

Decker et al., "Cell–Associated Tumour Necrosis Factor (TNF) as a Killing Mechanism of Activated Cytotoxic Macrophages," *J. Immunol.*, 138:957–962 (Feb. 1, 1987).

Kriegler et al., "A Novel Form of TNF/Cachetin Is a Cell Surface Cytotoxic Transmembrane Protein: Ramifications for the Complex Physiology of TNF," *Cell*, 53:45–53 (Apr. 8, 1988).

Folks et al., "Tumour necrosis factor α induces expression of human immunodeficiency virus in a chronically infected T–cell clone," *PNAS (USA)*, 86:2365–2368 (Apr. 1989).

(List continued on next page.)

*Primary Examiner*—Mindy Fleisher
*Assistant Examiner*—Nancy J. Degen
*Attorney, Agent, or Firm*—Donald J. Pochopien; Paul B. Savereide; Robert P. Blackburn

[57] ABSTRACT

Compositions and methods are described for identifying inhibitors of mature protein hormone formation from a prohormone, and prophylactic and therapeutic uses of the inhibitors for treating diseases associated with elevated levels of the mature hormones, particulary sepsis, AIDS and autoimmune diseases.

5 Claims, 3 Drawing Sheets

Biotin-peptide-spacer-cys

OTHER PUBLICATIONS

Elliot, et al., "Treatment of Rheumatoid Arthritis With Chimeric Antibodies to tumour Necrosis Factor α," *Arthritis & Rheumatism*, 36:1681–1690 (Dec. 1993).

Seckinger et al., "A Human Inhibitor of Tumour Necrosis Factor α," *J. Exp. Med.*, 167:1511–1516 (1988).

Seckinger et al., "Purification and Biologic Characterization of a Specific Tumour Necrosis Factor α Inhibitor," *J. Biol. Chem.*, 264:11966–11973 (1989).

Dinarello et al., "Multiple biological Activities of Human Recombinant Interleukin–1," *J. Clin. Invest.* 77:1734–1739 (1986).

Arend et al., "Effects of Immune Compleses on Production by Human Monocytes of Interleukin–1 or an Interleukin–1 Inhibitor," *J. Immunol.*, 134:3868–3975 (1985).

Seckinger et al., "A Urine Inhibitor of Interleukin–1 Activity that Blocks Ligand Binding," *J. Immunol.*, 139:1546–1549 (1987).

Hannum et al., "Interleukin–1 Receptor Antagonist Activity of a Human Interleukin–1 Inhibitor," *Nature*, 343:336–340 (1990).

Eisenberg et al., "Primary Structure and Expression from Complementary DNA of a Human Interleukin–1 Receptor Antagonist," *Nature*, 343:341–346 (1990).

Kostura et al., "Identification of a monocyte specifc pre–interleukin 1β convertase activity," *PNAS* (USA), 86:5227–5231 (Jul. 1989).

Scott et al., "Immunogenicity of Biotinylated Hapten–Avidin Complexes," *Molecular Immunology*, 21:1055–1060 (1984).

Tsuchiya et al., "Establishment and Characterization of a Human Acute Monocytic Leukemia Cell Line (THP-1)," *Int. J. Cancer*, 26:171–176 (1980).

Krakauer & Oppenheim, "Interleukin 1 Production by a Human Acute Monocytic Leukemia Cell Line," *Cell. Immunol.*, 80:223–229 (1983).

Silman & Katchalski, "Water–Insoluable Derivatives of Enzymes Antigens and Antibodies," *Ann. Rev. Biochem.*, 35:873–908 (1966).

Shadle et al., "Human Macrophage Colony–Stimulating Factor Heterogeneity Results From Alternative mRNA Splicing, Differential Glycosylation, and Proteolytic processing," *J. Cell. Biochem.*, 40:91–107 (1989).

Cseh et al., "Alternative Cleaveage of the Cachectin/TNF Propetide Results in a Larger, Inactive Form of Secreted Protein," *J. Biol. Chem.*, 264:16256–16260 (1989).

Merrifield, "Solid Phase Peptide Synthesis. I. The Synthesis of a Tetrapeptide," *J. Amer. Chem. Soc.*, 85:2149–2154 (Jul. 20, 1963).

Webb, "Arthritis Wonder Cure Wins Cautious Welcome," *New Scientist*, p. 16, (Feb. 12, 1994).

Elliott et al., "Treatment of Rheumatoid Arthritis with Chimeric Monoclonal Antibodies to Tumour Necrosis Factor α," *Arthritis & Rheumatism*, 36:1681–1690 (Dec. 1993).

Merrifield, "Solid Phase Synthesis," *Science* 232:341–347 (Apr. 18. 1986).

Beutler et al., "Passive Immunization Against Cachectin/Tumour Necrosis Factor Protects Mice from Lethal Effect of Endotoxin," *Science*, 229:869–871 (Aug. 30, 1985).

Ohlsson et al., "Interleukin–1 receptor antagonist reduces mortality from endotoxin shock," *Nature*, 348:550–552 (Dec. 6, 1990).

Pickup et al., "Suppression of Inflammatory Responses to Viral Infection: Viral Inhibition of the IL–1β Convertase," *J. Cell. Biochem.*, vol. 16, Supp. B, p. 285, Abstr. J217 (1992).

Sleath et l., "Substrate Specificity of the Protease That Processes Human Interleukin–1β," *J. Biol. Chem.*, 265:14526–14528 (Aug. 25, 1990).

Kobayashi et al., "Human Pre–interleukin 1α and β: Structural Features Revealed by Limited Proteolysis," *Chem. Pharm. Bull.*, 39:1513–1517 (Jun., 1991).

```
86  ATGAGCACTGAAAGCATGATCCGGGACGTGGAGCTGGCCGAGGAGGGCGCTCCCCAAGAAG  145
    ------+---------+---------+---------+---------+---------+
    MetSerThrGluSerMetIleArgAspValGluLeuAlaGluGluAlaLeuProLysLys

146 ACAGGGGGGCCCCAGGCTCCAGGCGGTGCTGTTCCTCAGCCTCTTCTCCTTCCTGATC    205
    ------+---------+---------+---------+---------+---------+
    ThrGlyGlyProGlnGlySerArgArgCysLeuPheLeuSerLeuPheSerPheLeuIle

206 GTGGCAGGCGCCACCACGCTCTTCTGCCTGCTCCACTTTGGAGTGATCGGCCCCAGAGG   265
    ------+---------+---------+---------+---------+---------+
    ValAlaGlyAlaThrThrLeuPheCysLeuLeuHisPheGlyValIleGlyProGlnArg

266 GAAGAGTCCCCCAGGACCTCTCTCTAATCAGCCCTCTGGCCCAGGCAGTCAGATCATCT   325
    ------+---------+---------+---------+---------+---------+
    GluGluSerProArgAspLeuSerLeuIleSerProLeuAlaGlnAlaValArgSerSer

326 TCTCGAACCCCGAGTGACAAGCCTGTAGCCCATGTTGTAGCAAACCCTCAAGCTGAGGGG  385
    ------+---------+---------+---------+---------+---------+
    SerArgThrProSerAspLysProValAlaHisValValAlaAsnProGlnAlaGluGly

386 CAGCTCCAGTGGCTGAACCGCCGGGCCAATGCCCTCCTGGCCAATGGCGTGGAGCTGAGA  445
    ------+---------+---------+---------+---------+---------+
    GlnLeuGlnTrpLeuAsnArgArgAlaAsnAlaLeuLeuAlaAsnGlyValGluLeuArg
```

FIG. 2C-1

```
446 GATAACCAGCTGGTGTGCCATCAGAGGGCCTGTACCTCATCTACTCCCAGGTCCTCTTC 505
       -----+---------+---------+---------+---------+---------+
       AspAsnGlnLeuValValProSerGluGlyLeuTyrLeuIleTyrSerGlnValLeuPhe

506 AAGGGCCAAGGCTGCCCCTCCACCACCATGTGCTCCCACCACCATCAGCCGCATCGCC 565
       -----+---------+---------+---------+---------+---------+
       LysGlyGlnGlyCysProSerThrHisValLeuLeuThrHisThrIleSerArgIleAla

566 GTCTCCTACCAGACCAAGGTCAACCTCCTCTGCCATCAAGAGCCCTGCCAGAGGGAG 625
       -----+---------+---------+---------+---------+---------+
       ValSerTyrGlnThrLysValAsnLeuLeuSerAlaIleLysSerProCysGlnArgGlu

626 ACCCCAGAGGGGCTGAGGCCAAGCCCTGTATGAGCCCATCTATCTGGGAGGGGTCTTC 685
       -----+---------+---------+---------+---------+---------+
       ThrProGluGlyAlaGluAlaAlaLysProTrpTyrGluProIleTyrLeuGlyGlyValPhe

686 CAGCTGGAGAAGGGTGACCGACTCAGCGCTGAGATCAATCGGCCCGACTATCTCGACTTT 745
       -----+---------+---------+---------+---------+---------+
       GlnLeuGluLysGlyAspArgLeuSerAlaGluIleAsnArgProAspTyrLeuAspPhe

746 GCCGAGTCTGGGCAGGTCTACTTTGGGATCATTGCCCTG
       -----+---------+---------+---------+
       AlaGluSerGlyGlnValTyrPheGlyIleIleAlaLeu
```

FIG. 2C-2

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
( A ) LENGTH: 23 amino acids
( B ) TYPE: amino acid
( D ) TOPOLOGY: linear (ii) MOLECULE TYPE: peptide (xi) SEQUENCE DESCRIPTION: SEQ ID NO:1:

Pro Leu Ala Gln Ala Val Arg Ser Ser Ser Arg Thr Pro Ser Asp Lys
1               5                   10                  15
Pro Val Ala His Val Val Ala
            20

(2) INFORMATION FOR SEQ ID NO:2:

(i) SEQUENCE CHARACTERISTICS:
    (A) LENGTH: 13 amino acids
    (B) TYPE: amino acid
    (D) TOPOLOGY: linear (ii) MOLECULE TYPE: peptide (xi) SEQUENCE DESCRIPTION: SEQ ID NO:2:

Arg Thr Pro Ser Asp Lys Pro Val Ala His Val Val Ala
1               5                   10

(2) INFORMATION FOR SEQ ID NO:3:

(i) SEQUENCE CHARACTERISTICS:
    (A) LENGTH: 13 amino acids
    (B) TYPE: amino acid
    (D) TOPOLOGY: linear (ii) MOLECULE TYPE: peptide (xi) SEQUENCE DESCRIPTION: SEQ ID NO:3:

Pro Leu Ala Gln Ala Val Arg Ser Ser Ser Arg Thr Pro
1               5                   10

(2) INFORMATION FOR SEQ ID NO:4:

(i) SEQUENCE CHARACTERISTICS:
    (A) LENGTH: 16 amino acids
    (B) TYPE: amino acid
    (D) TOPOLOGY: linear (ii) MOLECULE TYPE: peptide (xi) SEQUENCE DESCRIPTION: SEQ ID NO:4:

Gln Ala Val Arg Ser Ser Ser Arg Thr Pro Ser Asp Lys Pro Val Ala
1               5                   10                  15

(2) INFORMATION FOR SEQ ID NO:5:

(i) SEQUENCE CHARACTERISTICS:
    (A) LENGTH: 7 amino acids
    (B) TYPE: amino acid
    (D) TOPOLOGY: linear (ii) MOLECULE TYPE: peptide (xi) SEQUENCE DESCRIPTION: SEQ ID NO:5:

Gln Ala Val Arg Ser Ser Ser
1               5

(2) INFORMATION FOR SEQ ID NO:6:

(i) SEQUENCE CHARACTERISTICS:
    (A) LENGTH: 16 amino acids
    (B) TYPE: amino acid
    (D) TOPOLOGY: linear (ii) MOLECULE TYPE: peptide ( x i ) SEQUENCE DESCRIPTION: SEQ ID NO:6:

Gln Ala Val Arg Ser Ser Arg Thr Pro Ser Asp Lys Pro Val Ala
1               5                   10                  15

( 2 ) INFORMATION FOR SEQ ID NO:7:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

Ala Tyr Val His Asp Ala Pro Val Arg Ser
1               5                   10

( 2 ) INFORMATION FOR SEQ ID NO:8:

( i ) SEQUENCE CHARACTERISTICS:
        ( A ) LENGTH: 30 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 24..28
        ( D ) OTHER INFORMATION: /note= "The residue at this
            location is beta-alanine"

( x i ) SEQUENCE DESCRIPTION: SEQ ID NO:8:

Pro Leu Ala Gln Ala Val Arg Ser Ser Arg Thr Pro Ser Asp Lys
1               5                   10                  15

Pro Val Ala His Val Val Ala Xaa Xaa Xaa Xaa Xaa Cys Gly
            20                  25                  30

( 2 ) INFORMATION FOR SEQ ID NO:9:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 14..18
        ( D ) OTHER INFORMATION: /note= "The residue at this
            location is beta-alanine"

( x i ) SEQUENCE DESCRIPTION: SEQ ID NO:9:

Arg Thr Pro Ser Asp Lys Pro Val Ala His Val Val Ala Xaa Xaa Xaa
1               5                   10                  15

Xaa Xaa Cys Gly
            20

( 2 ) INFORMATION FOR SEQ ID NO:10:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site (B) LOCATION: 14..18
(D) OTHER INFORMATION: /note= "The residue at this location is beta-alanine"

(xi) SEQUENCE DESCRIPTION: SEQ ID NO:10:

```
Pro Leu Ala Gln Ala Val Arg Ser Ser Ser Arg Thr Pro Xaa Xaa Xaa
1               5                   10                  15
Xaa Xaa Cys Gly
            20
```

(2) INFORMATION FOR SEQ ID NO:11:

(i) SEQUENCE CHARACTERISTICS:
(A) LENGTH: 17 amino acids
(B) TYPE: amino acid
(D) TOPOLOGY: linear (ii) MOLECULE TYPE: peptide (ix) FEATURE:
(A) NAME/KEY: Modified-site
(B) LOCATION: 11..15
(D) OTHER INFORMATION: /note= "The residue at this location is beta-alanine"

(xi) SEQUENCE DESCRIPTION: SEQ ID NO:11:

```
Ala Tyr Val His Asp Ala Pro Val Arg Ser Xaa Xaa Xaa Xaa Xaa Cys
1               5                   10                  15
Gly
```

METHOD FOR DETERMINING TNF

This application is a continuation of U.S. Ser. No. 08/385,434, filed Feb. 8, 1995, now U.S. Pat. No. 5,545,518, which is a continuation of U.S. Ser. No. 08/053,558, filed Apr. 26, 1993, now U.S. Pat. No. 5,422,425, which is a continuation of U.S. Ser. No. 07/562,720, filed Aug. 6, 1990, now abandoned, each of which is incorporated herein by reference.

FIELD OF THE INVENTION

This invention is in the area of immunology/biochemistry, and particularly concerns the development of compositions and methods for identifying inhibitors of protein hormone formation, and prophylactic and therapeutic uses of the inhibitors for treating diseases associated with elevated levels of the hormones. More specifically, the invention facilitates the identification of compounds that may be used to treat a variety of diseases, particulary sepsis, AIDS and autoimmune diseases, and thus affords the physician alternate treatment regimes.

BACKGROUND OF THE INVENTION

In the United States alone nosocomial bacteremia develops in about 194,000 patients, and of these about 75,000 die. Maki, D. G., 1981, *Nosocomial Infect.*, (Dikson, R. E., Ed.), page 183, Yrke Medical Books, U.S.A. Most of these deaths are attributable to six major gram-negative bacilli, and these are *Pseudomonas aeruginosa, Escherichia coli*, Proteus, Klebsiella, Enterobacter and Serratia. The current treatment for bacteremia is the administration of antibiotics which, unfortunately, have limited effectiveness.

The precise pathology of bacteremia is not completely elucidated, nevertheless, it is known that bacterial endotoxins, lipopolysaccharides (LPS), are the primary causative agent. LPS consist of at least three significant antigenic regions, the lipid A, core polysaccharide, and O-specific polysaccharide. The latter is also referred to as O-specific chain or simply O-antigen. The O-specific chain region is a long-chain polysaccharide built up from repeating polysaccharide units. The number of polysaccharide units differs among different bacterial species and may vary from one to as many as six or seven monosaccharide units. While the O-specific chain varies among different gram-negative bacteria, the lipid A and core polysaccharides are similar if not identical.

Since LPS plays a key role in sepsis, a variety of approaches has been pursued to neutralize its activity. Presently, there is considerable work which suggest that antibody to LPS will soon be a valuable clinical adjunct to the standard antibiotic therapy.

LPS initiates a cascade of biochemical events that eventually causes the death of the patient. It is widely believed that the second event, after the introduction of LPS, is he production of tumor necrosis factor (TNF) as a result of LPS stimulation of macrophage cells. Thus, considerable effort has been expended to produce neutralizing antibody to TNF, or other molecules that could inhibit its septic effects. It is likely that antibody to TNF will have valuable clinical applications. Tracey, et al., 1987, *Nature*, 330:662.

TNF has been shown to exist in both membrane bound and soluble secreted forms. Decker, et al., 1987, *J. of Immunol.*, 138:957; Kriegler, et al., 1988, *Cell*, 53:45. Human TNF has been cloned and shown to consist of a 17 kD polypeptide, plus an unusually long 76 amino acid putative signal leader sequence. The 17 kD molecule is a key agent involved in initiating the biochemical cascade responsible for sepsis. It has been proposed by Kriegler, et al., 1988, *Cell*, 53:45, that TNF may exist as both a membrane bound 26 kD form, and a soluble form corresponding to the 17 kD species. The 26 kD form is the precursor, or prohormone, of the mature 17 kD molecule. It has further been proposed by Kriegler, et al. above, that the two forms of TNF may have different biological effects.

It will be appreciated that because TNF plays a key role in causing sepsis that there is a need to identify and develop anti-TNF prophylactics/therapeutics. As mentioned above, anti-TNF antibody appears to be promising, and has been shown to be effective in baboons. However, these studies have involved the use of non-human TNF and non-human TNF antibody. From a practical standpoint non-human anti-TNF antibody will have limited therapeutic application because of immunologic rejection of the antibody by a patient's immune system. Consequently, human antibody, or genetically engineered antibody consisting of the human constant region and the mouse variable region are preferred.

TNF, in addition to playing a critical role in sepsis, has recently been shown to be involved in initiating the expression of human immunodeficiency virus in human cells that carry latent virus. Folks et al., 1989, *PNAS (USA)*, 86:2365. Thus, preventing or inhibiting the formation of the 17 kD, or lower molecular weight forms of TNF would be a valuable prophylactic for the treatment of AIDS patients by preventing the expression of virus that is latent in the patient.

TNF also plays a role in various autoimmune diseases, particularly arthritis. Duff, et al., 1987, International Conference on Tumor Necrosis Factor and Related Cytotoxins, 175:10. Thus, compounds or methods for inhibiting TNF action will have considerable application for the treatment of a variety of diseases of immunologic origin.

In addition to antibody, other molecules with TNF inhibitory activity are being sought. Non-antibody TNF inhibitors are described by Seckinger, et al., 1988, *J. Exp. Med.*, 167:1511, and Seckinger, et al, 1989, *J. Biol. Chem.*, 264:11966, and in EPA 88830365.8, inventors Wallach, et al. The inhibitors are present in the urine of febrile patients, and have been purified and shown to have molecular weights of about 27,000–33,000. To date neither of the inhibitors have been shown to be effective in the treatment of sepsis.

From the foregoing discussion it is apparent that there is a need to identify and develop additional anti-TNF inhibitors, both antibody based or otherwise, that may be efficaciously applied in the treatment of sepsis.

In addition to TNF, IL-1 is thought to be involved in sepsis, and furthermore is believed to have multiple biological activities with the two most prominent being fever production and lymphocyte activation. For instance, IL-1 interaction with endothelial cells has been shown to enhance procoagulant activity and endothelial cell adhesiveness for leukocytes. Also, as a consequence of endotoxin exposure, IL-1 is thought to induce an inhibitor of tissue plasminogen activator which would exasperate the coagulation events occurring during an acute inflammatory reaction. Finally, IL-1 is thought to cause the production of platelet activating factor and arachidonic acid metabolites, both of which are involved in an organism's response to endotoxin. It is worth noting that platelet activating factor and arachidonic acid metabolites are also directly produced in response to endotoxin.

There are two forms of IL-1: IL-1α and IL-1β. Although these molecules share limited sequence homology they have similar biological activity. Dinarello, C. A., et al., 1986,

*Journal Clinical Invest.,* 77:1734. Both molecules have molecular weights of about 17.5 kD, and are produced from a precursor molecule with a molecular weight of about 31 kD.

Because IL-1 has pleiotropic biological activities, many of which adversely affect the organism, it would be expected that the molecule must be tightly regulated if it is not to be injurious. Indeed, there are several reports of IL-1 inhibitors that regulate the action of IL-1. IL-1 inhibitory activity has been reported in monocyte conditioned medium, wherein the monocytes are grown on adherent immune complexes. Arena, W. P., et al., 1985, *Journal of Immun.,* 134:3868. Additionally, an inhibitor has been reported to be present in urine. Seckinger, P., et al., 1987, *Journal of Immun.,* 139:1546. Lastly, a protein inhibitor, purified and cloned, that has interleukin-1 receptor antagonist activity has been reported. Hannum, et al., 1990, *Nature,* 343:336, and Eisenberg, S., et al., 1990, *Nature,* 343:341.

It is thus becoming apparent that aside from their normal biological functions, which have not been fully elucidated, cytokines are pathologically associated with systemic changes arising from infection and tissue injury as witnessed by the fact that TNF and IL-1, alone or in combination, can cause a shock state in animals that hemodynamically and hematologically is characteristic of septic shock in man caused by bacterial infection. Further, TNF and IL-1 also play a role in various autoimmune diseases, particularly arthritis. Duff, et al., 1987, *International Conference on Tumor Necrosis Factor and Related Cytotoxins,* 175:10. No doubt these and other cytokines will be found to play a role in diseases other than those mentioned above. Thus, it is highly desirable to identify inhibitors of the cytokines that can be used to control their undesirable biological effects.

SUMMARY OF THE INVENTION

The invention described herein presents methods and compositions for the identification of chemical inhibitors that inhibit the production of the mature form of a protein hormone, preferably of immunologic origin, from its prohormone precursor. These compositions are useful for preventing or treating diseases in patients associated with elevated circulating levels of the mature hormone.

A second object of the invention described herein relates to a method for identifying molecules that inhibit the production of the mature form(s) of TNF, and IL-1.

A third object of the invention is a description of a method that can be used to identify prophylactics and/or therapeutics for the treatment of sepsis premised on the ability of these medicaments to interfere with the cleavage of the prohormone form of various cytokines.

A fourth object of the invention is a description of a method that can be used to identify prophylactics and/or therapeutics for the treatment of sepsis premised on the ability of these medicaments to interfere with the cleavage of 26 kD TNF, or 31 kD IL-1 prohormones by an enzyme(s), termed convertase, that cleaves these molecules thereby producing lower molecular weight sepsis inducing molecules.

A fifth object of the invention is a description of a method that identifies inhibitors of sepsis that have significant prophylactic and/or therapeutic applications premised on the ability of the inhibitors to interfere with or prevent proteolysis of a peptide that has a convertase cleavage site present in the prohormone form of various cytokines.

A sixth object of the invention is a presentation of preferred prophylactics or therapeutics that inhibit cytokine convertase activity, and that are effective in treating sepsis.

These and further objects of the invention will become apparent after a full consideration of the detailed description of the invention shown below.

BRIEF DESCRIPTION OF THE DRAWINGS

FIGS. 2A-2C show the restriction map of the DNA sequence that encodes 26 kD TNF, a hydrophobicity plot of 26 kD TNF and the DNA and amino acid sequences of TNF, respectively.

DETAILED DESCRIPTION OF THE INVENTION

1. Definitions

Figure 1:
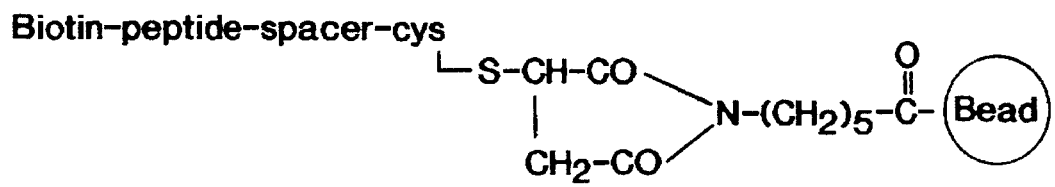
FIG. 1 shows the structure of a biotinylated peptide coupled to a solid matrix via an appropriate spacer moiety.

To facilitate understanding the nature and scope of applicant's invention, several definitions regarding various aspects of the invention are presented below. It will be understood, however, that these definitions are general in nature, and encompassed within the definitions are meanings well known to those skilled in the art.

The terms "prohormone", and "mature hormone" have the following meanings. Prohormone is intended to cover proteins, preferably of immunologic origin, that have a peptide segment of the protein removed during its in vivo production. The removal of the peptide yields the "mature" form of the hormone. The preferred embodiment of the invention is by way of example, the 26 kD TNF prohormone, as discussed in detail below, is cleaved primarily to a 17 kD mature form. Also, the 31 kD IL-1 prohormone is cleaved primarily to a 17.5 kD mature form. It is important to note, that prohormones in addition to TNF and IL-1 are intended to come within the scope of these definitions and are considered a part of the invention. For example, the CSFs are considered to come within the scope of the invention.

Sepsis is herein defined to mean a disease resulting from gram-positive or gram-negative bacterial infection, the latter primarily due to the bacterial endotoxin, lipopolysaccharide (LPS). It can be induced by at least the six major gram-negative bacilli and these are *Pseudomonas aeruginosa, Escherichia coli,* Proteus, Klebsiella, Enterobacter and Serratia. TNF and IL-1 are two factors that are detectable in the early phase of the disease, and that contributes to its progress.

As used herein, TNF having a molecular weight of about 26,000, refers to the prohormone form of TNF. It is known that the amino-terminal peptide of the prohormone varies in length depending on the species from which it is derived, while the propeptide segment of the molecule is highly conserved. Indeed, in the mouse approximately 86% of the 79 amino acids that makeup the putative leader sequence of the prohormone are identical to the 76 known amino acids that comprise the pro-sequence of human TNF. Thus, it will be appreciated by those skilled in the art that when reference is made below to TNF having a molecular weight of about 26,000, that what is indicated is a molecule that is not derived from a particular species and that may have a slightly altered leader sequence compared to the human sequence as is known in the art.

As used herein, IL-1 having a molecular weight of about 31 kD, refers to the prohormone form of IL-1. Kostura, M., et al., 1989, *PNAS (USA),* 86:5227. Thus, it will be appreciated by those skilled in the art that when reference is made to IL-1 that what is indicated is a molecule that is susceptible to cleavage via convertase action to a biologically active mature form.

The terms "TNF convertase", or "IL-1 convertase" are meant to encompass enzymes normally present in the body that are responsible for cleaving 26 kD TNF, or 31 KD IL-1.

The instant invention concerns methods and compositions for identifying inhibitors of diseases associated with the production of mature hormones from their prohormone forms. The preferred embodiment of a prohormone is 26 kD TNF, which is cleaved to lower molecular weight molecules, particularly one having a molecular weight of 17 kD, that are substantially involved in producing sepsis. Thus, inhibitors capable of interfering with the conversion of the 26 kD form of TNF are useful for preventing or treating sepsis.

The assays described herein detect chemicals that inhibit or retard the conversion of a prohormone to its mature hormone form, with the preferred embodiment being the enzymatic conversion of the 26 kD molecular weight form of TNF to, preferably, a 17 kD molecular weight form. The assay is premised on the recognition by the convertase of a particular amino acid sequence associated with the prohormone that upon cleavage of the molecule yields the mature form. Various peptides have been synthesized that exhibit these cleavage sites and are employed in assays to identify inhibitors of the enzyme.

Preferably the peptides are attached to a solid surface. The peptides are labelled, as will be described more below, such that after reaction with convertase enzyme they are hydrolyzed into one or more smaller peptides that carry the label. Inhibitors of the enzyme are identified by their ability to interfere with the activity of the convertase enzyme and thus prevent or retard hydrolysis of the peptide substrate into its smaller component labelled peptides. Thus, molecules that do not have inhibitory activity do not affect the activity of the enzyme and result in the release of labelled peptide, whereas inhibitors of the enzyme prevent or retard the release of labelled peptides. Consequently, inhibitors are readily identified by measuring the amount of label that is released, or that remains associated with the peptide substrate after treatment with the convertase.

The invention is most readily presented in four parts. Part one shows the materials and methods for realizing peptides, both TNF and IL-1, that are susceptible to convertase cleavage. Part two identifies sources of TNF and IL-1 convertases, and methods for partially purifying the enzymes that may be used to assay for inhibitors. Part three describes assays for detecting and identifying various TNF and IL-1 convertase inhibitors. Finally, part four of the invention presents a description of ways of using the inhibitors to treat patients suffering from sepsis. Each of these sections will now be addressed separately.

Several patents/patent applications and scientific references are referred to below. The instant invention draws on some of the materials and methods shown in these references, and thus it is intended that all of the references, in their entirety, be incorporated by reference.

I. Peptides Susceptible to Cleavage by Cytokine Convertases

Regarding the conversion of the 26 kD TNF molecule, the convertase, as will become apparent below, cleaves the molecule at one internal site, and perhaps at several. The major site is at the junction which separates the secreted form of TNF, that is, the 17 kD molecular weight species, from the leader sequence. The sequence at this junction is -Gln-Ala-Val-Arg-Ser-Ser-. Thus, the major cleavage event occurs between alanine and valine, since valine is known to be the amino terminal amino acid of the 17 kD molecular weight molecule. Several other species of TNF are produced by the convertase, and thus these are the products of secondary cleavage sites. Regardless of whether the 26 kD molecule is cleaved at one or more sites, insofar as the identification of therapeutics/prophylactics of sepsis is concerned this is of marginal concern since the instant assay can monitor either the inhibition of the conversion of the 26 kD TNF species, or the appearance of a lower molecular weight form.

Since the amino acids that are cleaved are Ala-Val, peptides having these two amino acids plus an appropriate number of corresponding amino terminal carboxyl terminal amino acids that are representative of those found in the 26 kD TNF molecule should be appropriate substrates to assay convertase activity.

Preferred peptide constructs would include the following:

1. Pro-Leu-Ala-Gln-Ala-Val-Arg-Ser-Ser-Ser-Arg-Thr-Pro-Ser-Asp-Lys-Pro-Val-Ala-His-Val-Val-Ala [SEQ ID NO:1];
2. Arg-Thr-Pro-Ser-Asp-Lys-Pro-Val-Ala-His-Val-Val-Ala [SEQ ID NO:2]; and
3. Pro-Leu-Ala-Gln-Ala-Val-Arg-Ser-Ser-Ser-Arg-Thr-Pro [SEQ ID NO:3].

An alternate embodiment of a peptide substrate is one that has an amino acid sequence that is functionally similar to: Gln-Ala-Val-Arg-Ser-Ser-Ser-Arg-Thr-Pro-Ser-Asp-Lys-Pro-Val-Ala [SEQ ID NO:4]. This peptide spans both TNF convertase cleavage sites. The first, and dominant cleavage site is between alanine and valine at positions −1 and +1; and the second site is between proline and valine at positions +12 and +13. These positions correspond to the amino acid sequence shown in FIG. 1.

Another class of substrates consists of compounds having a partial sequence of the peptides shown above; that is, Gln-Ala-Val-Arg-Ser-Ser-Ser [SEQ ID NO:5], or Gln-Ala-Val-Arg-Ser-Ser-Ser-Arg-Thr-Pro-Ser-Asp-Lys-Pro-Val-Ala [SEQ ID NO:6].

The preferred embodiment peptide substrate for IL-1 convertase(s) has the amino acid sequence as follows:

Ala-Tyr-Val-His-Asp$_{116}$-Ala$_{117}$-Pro-Val-Arg-Ser [SEQ ID NO:7]

The IL-1 convertase(s) cleaves the IL-1β prohormone between the amino acid residues underlined above, that is, between Asp$_{116}$ and Ala$_{117}$.

The TNF and IL-1 peptides described above can be made by techniques well known in the art, such as, for example, the Merrifield solid-phase method described in *Science*, 1985, 232:341–347. The procedure may use commercially available synthesizers such as a Biosearch 9500 automated peptide machine, with cleavage and deprotection of the peptide being achieved with hydrogen fluoride, and the peptides purified by preparative HPLC using a Waters Delta Prep 3000 instrument, on a 15–20 μm Vydac C18 PrepPAK column.

Finally, it is important to be cognizant of the fact that the specificity of the TNF convertase is similar to enzymes like elastase, that is, enzymes that cleave preferably between neutrally charged amino acids such as between valine, proline, and alanine residues. Thus, in addition to the peptide substrates mentioned above, a variety of other substrates having properly ordered neutrally charged amino acids can be readily constructed and utilized in the assay described herein.

To facilitate using the peptides in assays aimed at detecting convertase activity, or inhibitors of convertase, the peptides can be modified to carry a label which would be detectable as a function of convertase activity, which is discussed more below, or additionally by incorporation of spacer groups that would facilitate exposing the cleavage site residues to the enzyme, that is, Ala-Val and Asp-Ala in the case of TNF and IL-1, respectively. A variety of amino acids are utilized as spacer groups and these are known in the art. Preferably the spacer groups would include D or L-alanine or proline, or β-alanine. A spacer group consisting of proline would have the property of being relatively rigid, while a beta-alanine spacer, because of its lack of ordered structures, would be more flexible. The position and number of such spacer groups can be determined empirically; however, preferably these spacer groups will be at or near the carboxyl terminal end of the molecule, and therefore a distance away from the Ala-Val primary cleavage site of TNF and the Asp-Ala cleavage site of IL-1. Preferably the number of amino acids that form the spacer will be between about 5 and 8.

It is important to note that although the preferred embodiment spacer groups have been defined above, more generally the spacer group comprises any sequence of amino acids that exhibit one of two non-mutually exclusive properties. Firstly, the spacer may be described as having one or more extended structural regions that are linked by segments that exhibit a significant degree of flexibility. That is, each end of the spacer group may terminate with a flexible segment. In this instance, the spacer group links the convertase substrate to a solid substratum by way of suitable attachment amino acids or groups. This type of spacer is formed from a series of extended structure portions in tandem with intermediate flexible regions. As alluded to above, the extended, rigid portion(s) of the spacer is preferably formed from a series of proline amino acids, while the flexible portions are preferably composed of serine, glycine, or threonine amino acids.

Secondly, the spacer can be described in functional terms as being unreactive (i.e., not hydrolyzed) by proteases. Thus, the spacer preferably lacks the cleavage site amino acids present in TNF or IL-1.

An additional modification that may be desirable to incorporate into the peptides or spacer groups is an amino acid that exhibits a reactive group that would facilitate covalent bonding of the peptides, directly or indirectly, to a solid surface thereby facilitating the convertase assay. An exemplary reactive group would be a sulfhydryl group, preferably a sulfhydryl group exhibited by a cysteine amino acid.

Thus, with the above modifications to the peptides in mind, the most preferred peptides are those shown below. The peptides are represented with biotin as the label. Biotin binds strepavidin which in turn can be detected using methods known in the art. Biotin may be attached on the last N-terminal amino acid of the peptides using known chemical synthesis methods, which are discussed more below, and by Scott, Nitecki, Kindler, and Goodman, 1984, *Molecular Immunology*, 21:1055.

The preferred spacer groups associated with the peptides are β-alanine, and the reactive group is a sulfhydryl group of cysteine. It will be noted that the spacer group is shown as consisting of five β-alanine residues; however, as alluded to above, it will be appreciated by those skilled in the art that fewer or lesser residues may perform satisfactorily and the exact number is easily ascertainable and within the skill of the practitioner in this field.

TNF Peptides

1. Biotin-Pro-Leu-Ala-Gln-Ala-Val-Arg-Ser-Ser-Ser-Arg-Thr-Pro-Ser-Asp-Lys-Pro-Val-Ala-His-Val-Val-Ala-(beta-ala)$_5$-cys-gly [SEQ ID NO:8];

2. Biotin-Arg-Thr-Pro-Ser-Asp-Lys-Pro-Val-Ala-His-Val-Val-Ala-(beta-ala)$_5$-cys-gly [SEQ ID NO:9]; and 3. Biotin-Pro-Leu-Ala-Gln-Ala-Val-Arg-Ser-Ser-Ser-Arg-Thr-Pro-(beta-ala)$_5$-cys-gly [SEQ ID NO:10];

IL-1 Peptide

1. Ala-Tyr-Val-His-Asp-Ala-Pro-Val-Arg-Ser-(beta-ala)$_5$-cys-gly [SEQ ID NO:11].

Figure 2A:
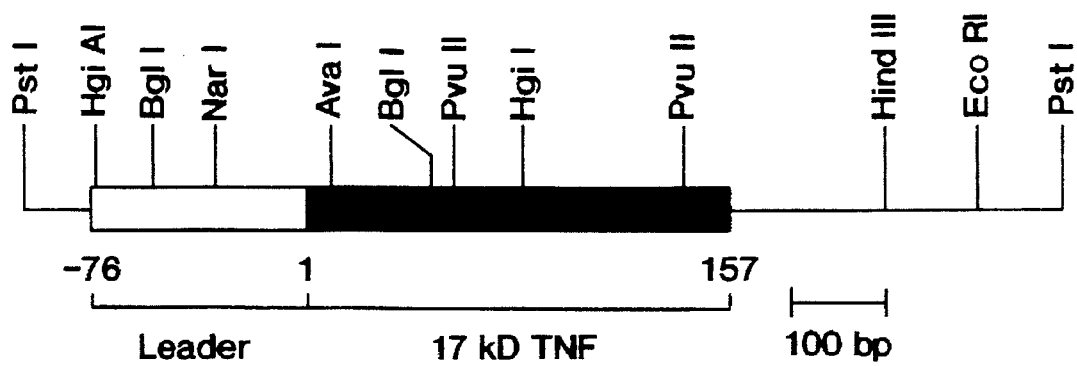
Figure 2B:
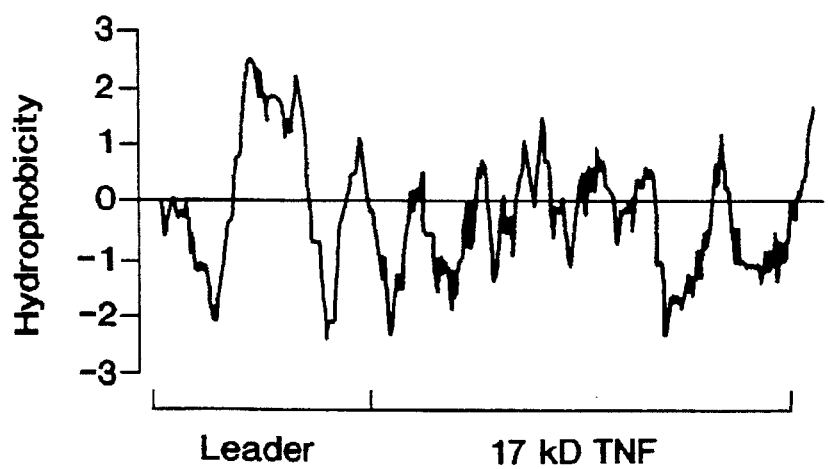

FIG. 2 presents the preferred embodiment biotinylated peptide constructs affixed to a solid matrix via the SH group on the cysteine amino acid.

II. Convertase

A variety of biological materials are available as sources of TNF or IL-1 convertase activity. These include tissues, cells, or extracts, or fluids associated therewith that are preferably, but not necessarily, of immunologic origin. Moreover, established cell lines may also be utilized. Suitable sources for TNF convertase would include human peripheral blood mononuclear cells, such as leukocytes or cell lines of leukocyte origin, preferably the cell line HL60 or U937. Because of the ease of manipulating established cell lines, the preferred source of the convertase is HL60 or U937. Thus, the cleavage of the peptides described in Section I may be performed with either intact HL60 cells, extracts derived therefrom, or any other suitable source of the convertase. In some cell types, TNF convertase activity is present in the culture medium after the appropriate stimulation, which is discussed more below, thus cell culture media could be used as a source of the convertase. Further, because the convertase activity is partially membrane associated, it is possible to obtain a membrane fraction that may be utilized.

The procedures for isolating monocytes are well known in the art, as are other methods for culturing cell lines such as HL60 or U937. Briefly, monocytes may be prepared from peripheral blood by centrifugation first through Ficoll-paque and percoll (49.2%) using standard procedures. This yields an enriched population of monocytes and lymphocytes, and the monocytes can be further enriched by plating the mixture of cells onto tissue culture dishes and incubating the cells for a time sufficient to permit the monocytes to adhere to the surface of the dishes. The lymphocytes are then washed off of the plates leaving only adherent monocytes. These cells may then be used as is, or can be stimulated to produce enhanced levels of convertase using known monocyte activators, preferably lipopolysaccharide and phorbol myristate acetate. The cells may be fractionated, and either an extract or a membrane fraction prepared therefrom and employed in the assays described below.

Il-1 convertase activity is also found in monocytes, and a preferred source of the enzyme is human blood monocytes. Cell lines also produce the enzyme, particularly cell lines that have monocyte like properties, such as human THP.1 cells that are on deposit with the American Type Culture Collection, and are described by Tsuchiya, S., et al., 1980, *Int. J. Cancer*, 26:171; and Krakauer, T. and Oppenheim, J., 1983, *Cell. Immunol.*, 80:223.

IL-1 convertase activity may be obtained from cell extracts prepared essentially as described by Kostura, M., et al., above. Briefly, this involves preparing the enzyme from human peripheral blood monocytes or THP.1 after lysis of the cells as follows. The cells are washed using standard techniques, preferably by exposure to a hypotonic buffer containing 10 mM KCl, 20 mM HEPES, pH 7.4, 1.5 mM MgCl$_2$, 0.1 mM EDTA. After 20 minutes on ice in 3 volumes of this buffer, the cells are homogenized using a standard Dounce homogenizer until all the cells are broken. The resulting homogenates may be clarified by low speed centrifugation, and the resulting supernatant (S-1) fractionated by high speed centrifugation. This would consist of centrifuging the S-1 supernatant at 30,000×g to obtain a S-30 supernatant. This supernatant is then centrifuged at 300,000×g to obtain a S-300 supernatant. The latter two centrifugations are done using standard centrifugation methods and rotors, and are conducted at 4° C. For example, the 300,000×g centrifugation is typically conducted for 1.5 hours at 4° C. in a Beckman type 50.2 rotor. The S-300 cell free extracts contain IL-2β convertase activity, and aliquots may be used to assay for inhibitor of IL-1 hormone formation from the prohormone. It is noteworthy that IL-1β activity is present in the other cellular fractions and these may be utilized as well.

III. Identification of Inhibitors of Convertase Activity-Prophylactics or Therapeutics of Sepsis Inhibitors of convertase activity will also be prophylactics or therapeutics that may be used in the treatment of sepsis. They may be identified using the foregoing assay, and further including in the assay reaction mixture compounds sought to be tested for inhibitory activity. A suitable assay would consist of combining one or more of the peptides discussed above, the convertase, and a putative inhibitor. The appropriate controls will be performed including running the reaction without convertase and/or chemicals sought to be tested for inhibitory activity.

More specifically, as mentioned above, inhibitors of the enzyme are identified by their ability to interfere with convertase activity, and thus prevent or retard hydrolysis of the peptide substrates into smaller component labelled peptides. Thus, molecules that do not have inhibitory activity do not affect the activity of the enzyme and result in the release of labelled peptide, whereas inhibitors interfere with the activity of the enzyme, and thus prevent or retard the release of labelled peptide. Consequently, inhibitors are identified by preferably measuring the amount of label that remains associated with the substrate peptide after treatment with convertase.

It will be understood by those skilled in the art that the inhibitory material may be added to the convertase before the convertase is added, or it can be added prior to, or immediately after adding the convertase. The order of addition may facilitate identification of inhibitors, but it is not determinative. Thus, the conditions under which the appropriate peptide and convertase are combined do not constitute characteristic features of the invention, and will vary according to determinations to be carried out by the practitioner and will depend especially on the optimum temperatures, pH, activity of the convertase preparations, as well as other factors. These determinations can be carried out in accordance with experimental modalities which are easily understood by those skilled in the art.

The preferred embodiment assay is premised on the convertase reducing or eliminating biotin from the beads by cleaving the peptide at a site that releases the biotinylated part of the peptide from the beads. Thus, the assay is conducted by selecting a time point during the reaction that corresponds to the removal of most or all of the biotinylated residues. Inhibitors of the convertase effectively prevent the biotin moiety from being removed from the peptide, and thus the presence of biotin indicates an inhibitor of the enzyme.

The peptides employed in the present invention can be immobilized on any appropriate solid test support by any appropriate technique. The solid test support can be any suitable insoluble carrier material for the binding of antibodies and immunoassays. Many such materials are known in the art, including, but not limited to, nitrocellulose sheets or filters; agarose, resin, plastic (e.g. PVC or polystyrene) latex, or metal beads; plastic vessels; and the like. Many methods of immobilizing antibodies are also known in the art. See, e.g., Silman et al., 1966, Ann. Rev. Biochem., 35: 873; Melrose, 1971, Rev. Pure & App. Chem., 21: 83; Cuatrecaas et al., 1971, Meth. Enzym., 22. Such methods include covalent coupling, direct adsorption, physical entrapment, and attachment to a protein-coated surface. In the latter method, the surface is first coated with a water-insoluble protein such as zein, collagen, fibrinogen, keratin, glutelin, etc. Any combination of support and binding technique which leaves the peptide reactive can be employed in the present invention. A preferred solid test support is a plastic bead.

As discussed above, the assay of the present invention employs a label attached to the peptide substrate such that cleavage of the peptide produces a smaller peptide that has the label associated with it. The label can be detected and monitored as a function of convertase activity, and can be any type that allows for the detection of convertase activity. Generally, the label directly or indirectly results in a signal which is measurable and related to the amount of label present in the sample. For example, directly measurable labels can include radio-labels (e.g. $^{125}$I, $^{35}$S, $^{14}$C, etc. A preferred directly measurable label is an enzyme, conjugated to a molecule that binds to a region of the peptide substrate. The enzyme would produce a color reaction in the presence of the appropriate substrate (e.g. horseradish peroxidase/o-phenylenediamine). An example of an indirectly measurable label is peptide that has been biotinylated. The presence of this label is measured by contacting it with a solution containing a labelled avidin complex, whereby the avidin becomes bound to the biotinylated peptide. The label associated with the avidin is then measured. A preferred example of an indirect label is the avidin/biotin system employing an enzyme conjugated to avidin, the enzyme producing a color reaction as described above.

Whatever label is selected, it results in a signal which can be measured and is related to the amount of label in a sample. Common signals are radiation levels (when radio-isotopes are used), optical density (e.g. when enzyme color reactions are used) fluorescence (when fluorescent compounds are used) and chemiluminescence (when chemiluminescent compounds are used). It is preferred to employ a nonradioactive signal, such as optical density (or color intensity) produced by an enzyme reaction. Numerous enzyme/substrate combinations are known in the immunoassay art which can produce a suitable signal. See, e.g., U.S. Pat. Nos. 4,323,647 and 4,190,496, the disclosures of which are incorporated herein.

IV. Treatment of Disease

Compounds identified as having convertase inhibitory activity will also have prophylactic or therapeutic applications in the treatment of sepsis. Because the onset of sepsis is associated with an increase in circulating TNF or IL-1, these inhibitors may be used prophylactically in those instances where there is a risk of bacterial infection, particularly in a pre-operative setting. Similarly, in those instances where there is an early diagnosis of sepsis, the inhibitors will have beneficial therapeutic effects in substantially reducing the amount of TNF that is produce.

A second medical application for inhibitors of convertase is for the treatment of AIDS. It has been shown that TNF causes the activation of latent human immunodeficiency virus. Folks et al., 1989, PNAS (USA), 86:2365. Thus, preventing or inhibiting the formation of the 17 kD, or lower molecular weight forms of TNF by inhibition of the convertase would be a valuable prophylactic for the treatment of AIDS, and would preferable be used to treat patients that are infected with the virus that is in a latent phase.

Having generally described what the applicants believe their invention to be, presented below are examples that are illustrative of the scope of the invention. It will be appreciated by those skilled in the art that the examples are not intended to be construed as limiting the invention to the materials and methods shown as there are numerous substitutions that can be made therein without departing from the scope of the invention.

EXAMPLE 1

Synthesis of Peptide Substrates

The following three biotin labelled peptides were synthesized:

1. Biotin-Pro-Leu-Ala-Gln-Ala-Val-Arg-Ser-Ser-Ser-Arg-Thr-Pro-Ser-Asp-Lys-Pro-Val-Ala-His-Val-Val-Ala-(beta-ala)$_5$-cys-gly [SEQ ID NO:8];
2. Biotin-Arg-Thr-Pro-Ser-Asp-Lys-Pro-Val-Ala-His-Val-Val-Ala-(beta-ala)$_5$-cys-gly [SEQ ID NO:9]; and
3. Biotin-Pro-Leu-Ala-Gln-Ala-Val-Arg-Ser-Ser-Ser-Arg-Thr-Pro-(beta-ala)$_5$-cys-gly [SEQ ID NO:10];

The peptides were synthesized using Merrifield's solid-state method described in *J. Amer. Chem. Soc.*, 1963, 75:48–79. A Biosearch 9500 automated peptide machine was employed with t-Boc amine protection. The peptides were cleaved with hydrogen fluoride, and purified by preparative HPLC on a Waters Delta Prep 3000 with a PrePAK C18 column and an aqueous-acetonitrile-trifluoroacetic acid mobile phase. Biotin was attached on the last N-terminal amino acid on the resin using known methods. Scott, Nitecki, Kindler, and Goodman, 1984, *Molecular Immunology,* 21:1055. The peptides were cleaved from the resin with liquid hydrogen fluoride since it does not adversely affect the biotinyl residue on the peptide.

EXAMPLE 2

Method of Coupling Biotinylated Peptides to a Solid Matrix

The biotinylated peptide shown above would be attached to a solid matrix by derivatizing amino-containing beads with maleimido-6-amino caproyl-HNSA cross-linking agent, which generates maleimido groups on the beads. Suitable beads may be obtained from Sigma, Biorad, Pharmacia. Subsequently the beads are reacted with the biotinylated peptides and via the SH group of cysteine the peptide adds onto the maleimido ring and forms a covalent bond thereto.

More specifically, Sepharose 4B beads (Sigma Corp.) having omega-aminohexyl groups are swelled in 0.1M phosphate buffer, pH 7.5. Next, a 3-fold molar excess of maleimido-6-amino-caproyl-HNSA over amine groups added and monitored for anion release as is known in the art. Shadle, P. J., Aldwin, L., Nitecki, D. E., and Koths, K., 1989, *J. of Cell Biochem.,* 40:91. When it is apparent that the reaction is completed, usually within 30 minutes, the gel is washed extensively with 0.1M phosphate buffer, pH 6.0. When the yellow color has all been eluted, a 2-fold molar excess of the peptide over gel amino groups is added. Next, the mixture is rocked gently at 4° C. for 24 hours, which is sufficient time to react the SH groups on the cysteine residues of the peptides with the maleimide groups on the resin. The gel is washed to remove uncoupled peptide, and stored at 4° C. in phosphate buffer saline with an appropriate amount of sodium azide to retard bacterial growth.

EXAMPLE 3

Assay for Convertase Inhibitors

Inhibitors of convertase activity can be assayed by combining a source of convertase with a biotinylated peptide attached to solid affigel beads as described above, in the presence or absence of a compound sought to be tested for inhibitory activity. The assay is premised on the convertase reducing or eliminating biotin from the beads by cleaving the peptide at a site that releases the biotinylated part of the peptide from the beads. Thus,the assay is conducted by selecting a time point during the reaction that corresponds to the removal of most or all of the biotinylated residues. Inhibitors of the convertase effectively prevent the biotin moiety from being removed from the peptide, and thus the presence of biotin indicates an inhibitor of the enzyme. Biotin is detected using labelled avidin as is known in the art.

The reaction is conducted under appropriate reaction conditions, paying particular attention to the temperature, pH, ionic strength and co-factor requirements of the convertase used in the assay. At different times during the reaction period, aliquots of the solid matrix are removed, washed with a suitable wash solution, and the beads assayed for the presence of biotinylated peptide using a labelled biotin binding molecule, preferably avidin or strepavidin. The presence of a convertase inhibitor is indicated by binding of the labelled biotin binding molecule to the matrix associated peptide substrate when compared to control samples that lack the inhibitor.

We claim:

1. A method for identifying prophylactics or therapeutics of a disease caused by a mature protein hormone produced by convertase cleavage of a prohormone, said cleavage occurring at one or more amino acid sites of said prohormone, comprising the steps of:

a) synthesizing a peptide selected from the group consisting of Pro-Leu-Ala-Gln-Ala-Val-Arg-Ser-Ser-Ser-Arg-Thr-Pro-Ser-Asp-Lys Pro-Val-Ala-His-Val-Val-Ala (SEQ ID NO: 1), Arg-Thr-Pro-Ser-Asp-Lys-Pro-Val-Ala-His-Val-Val-Ala (SEQ ID NO: 2), Pro-Leu-Ala-Gln-Ala-Val-Arg-Ser-Ser-Ser-Arg-Thr-Pro (SEQ ID NO: 3), Gln-Ala-Val-Arg-Ser-Ser-Ser-Arg-Thr-Pro-Ser-Asp-Lys-Pro-Val-Ala (SEQ ID NO: 4), Gln-Ala-Val-Arg-Ser-Ser-Ser (SEQ ID NO: 5) and Ala-Tyr-Val-His-Asp-Ala-Pro-Val-Arg-Ser (SEQ ID NO: 7), said peptide being labelled;

b) contacting said peptide in a first sample with an effective amount of said convertase as a control to cleave said peptide into a fragment of fragments having the label;

c) contacting said peptide and a molecule sought to be identified as a prophylactic or therapeutic of a disease caused by said mature hormone in a second sample with an effective amount of said convertase as a control to cleave said peptide into a fragment of fragments having the label;

d) comparing the cleavage of the labelled peptide from steps b) and c), whereby a decrease in cleavage in step c) compared to step b) identifies said molecule as a prophylactic or therapeutic for said disease.

2. The method as described in claim 1, wherein the prohormone is a cytokine.

3. The method as described in claim 2, wherein said cytokine is selected from the group consisting of tumor necrosis factor (TNF) and interleukin-1 (IL-1).

4. The method as described in claim 3, wherein said cytokine is TNF.

5. The method as described in claim 3, wherein said cytokine is IL-1.

* * * * *

UNITED STATES PATENT AND TRADEMARK OFFICE
CERTIFICATE OF CORRECTION

PATENT NO. : 5,639,593

DATED : June 17, 1997

INVENTOR(S) : Michael Kriegler and Danute E. Nitecki

It is certified that error appears in the above-identified patent and that said Letters Patent is hereby corrected as shown below: On title page, item [73]

Please change the Assignee name "Cetus Oncology Corporation"

The Assignee name will read as follows:

Chiron Corporation, Emeryville, California

Signed and Sealed this

Twenty-first Day of April, 1998

*Attest:*

BRUCE LEHMAN

*Attesting Officer*     *Commissioner of Patents and Trademarks*